(12) United States Patent
Tordini et al.

(10) Patent No.: US 11,395,769 B2
(45) Date of Patent: Jul. 26, 2022

(54) DEVICE FOR APPLYING SEGMENTS OF ABSORBENT ARTICLES

(71) Applicant: GDM S.p.A., Bologna (IT)

(72) Inventors: Federico Tordini, Pedrengo (IT); Matteo Piantoni, Albino (IT)

(73) Assignee: GDM S.P.A., Bologna (IT)

( * ) Notice: Subject to any disclaimer, the term of this patent is extended or adjusted under 35 U.S.C. 154(b) by 232 days.

(21) Appl. No.: 16/645,257

(22) PCT Filed: Sep. 18, 2018

(86) PCT No.: PCT/IB2018/057174
§ 371 (c)(1),
(2) Date: Mar. 6, 2020

(87) PCT Pub. No.: WO2019/058256
PCT Pub. Date: Mar. 28, 2019

(65) Prior Publication Data
US 2020/0229986 A1     Jul. 23, 2020

(30) Foreign Application Priority Data
Sep. 20, 2017   (IT) .................. 102017000105328

(51) Int. Cl.
*A61F 13/15* (2006.01)
*B65H 35/08* (2006.01)

(52) U.S. Cl.
CPC .. *A61F 13/15764* (2013.01); *A61F 13/15723* (2013.01); *A61F 13/15699* (2013.01);
(Continued)

(58) Field of Classification Search
CPC ...................................................... B65H 3/40
See application file for complete search history.

(56) References Cited

U.S. PATENT DOCUMENTS

| 2003/0021619 A1* | 1/2003 | Johnson | B41J 3/54 |
| | | | 399/388 |
| 2013/0035222 A1* | 2/2013 | Andrews | A61F 13/15723 |
| | | | 493/342 |

(Continued)

FOREIGN PATENT DOCUMENTS

| CN | 104220032 A | 12/2014 |
| CN | 104670966 A | 6/2015 |

(Continued)

OTHER PUBLICATIONS

International Search Report and Written Opinion dated Nov. 9, 2018 for counterpart International Application No. PCT/IB2018/057174.

(Continued)

*Primary Examiner* — Barbara J Musser
(74) *Attorney, Agent, or Firm* — Shuttleworth & Ingersoll, PLC; Timothy J. Klima

(57) ABSTRACT

A device for applying segments of absorbent articles includes a cutting station for cutting a continuous web into segments and an applicator station for applying each segment on a respective absorbent article. A plurality of carrier units, each includes a pad for retaining and transferring a segment from the cutting station to the applicator station. The pad fully rotates about a main axis to transfer the segment from the cutting station to the applicator station and return to the cutting station and, from the cutting station to the applicator station, rotates at least 90° about its axis of rotation to orient the segment transverse to the feed direction of the absorbent article. A first movement member moves one or more first carrier units about the main axis and a second movement member moves one or more second carrier units separately from the first carrier units about the main axis.

10 Claims, 4 Drawing Sheets

(52) U.S. Cl.
CPC ............... *A61F 13/15756* (2013.01); *A61F 2013/15821* (2013.01); *B65H 35/08* (2013.01); *B65H 2801/57* (2013.01)

(56) References Cited

U.S. PATENT DOCUMENTS

| | | | |
|---|---|---|---|
| 2013/0239764 A1* | 9/2013 | McCabe | B65H 35/08 83/100 |
| 2014/0005019 A1 | 1/2014 | Hargett et al. | |
| 2015/0297416 A1 | 10/2015 | Piantoni et al. | |
| 2016/0354258 A1 | 12/2016 | Findley et al. | |

FOREIGN PATENT DOCUMENTS

| | | |
|---|---|---|
| CN | 104812350 A | 7/2015 |
| CN | 106236395 A | 12/2016 |
| CN | 106420182 A | 2/2017 |
| EP | 1415628 A1 | 5/2004 |
| WO | 2015079367 A1 | 6/2015 |

OTHER PUBLICATIONS

Chinese Office Action dated Apr. 15, 2021 from counterpart Chinese Patent Application No. 201880060736.4.

\* cited by examiner

DEVICE FOR APPLYING SEGMENTS OF ABSORBENT ARTICLES

This application is the National Phase of International Application PCT/IB2018/057174 filed Sep. 18, 2018 which designated the U.S.

This application claims priority to Italian Patent Application No. IT 102017000105328 filed Sep. 20, 2017, which application is incorporated by reference herein.

TECHNICAL FIELD

This invention relates to a device for applying segments of absorbent articles.

More specifically, but without thereby losing in generality, this device addresses the application field of processing a continuous web of elasticized material used to make the elasticized waistbands of nappies for children or adults.

The device of the invention makes, transfers, orients and applies a single segment of absorbent article in a continuous row of nappies being made.

BACKGROUND ART

Usually, prior art devices of this kind comprise a drum which is mounted for rotation about a respective main axis of rotation and which supports a plurality of anvils that act in conjunction with a cutting means to divide the continuous web into individual segments. Connected to the drum are a plurality of pads, each interposed between two respective anvils, capable of receiving the continuous web to be cut and retaining a respective segment resulting from cutting the continuous web itself.

Besides rotating about the main axis of rotation of the drum, each pad can rotate on itself about its own axis of rotation, which is disposed along a direction radial to the axis of rotation of the drum, in order to orient the respective segment in a direction transverse to the feed direction of the continuous row of nappies being made.

Also, in order to avoid collision with the anvils between which it is interposed during rotation about its main axis, each pad is movable away from the main axis of rotation of the drum, moving to a position substantially tangent to the nappies on which the segment being held is to be applied.

Each pad is movable towards the axis of rotation of the drum to return to the position for picking up a segment.

At present, market demands in the field of machinery for making absorbent articles require machines that are better performing and more flexible than machines known in the prior art. With reference to the device for applying segments of absorbent articles, these demands translate as higher production speed and the possibility of improved change-over features to minimize or cancel the down times for replacing machine components when changing over from making articles of one size to making articles of another size.

DISCLOSURE OF THE INVENTION

Hence the need is felt for a device for applying segments of absorbent articles, comprising a cutting station for cutting a continuous web into individual segments and an applicator station for applying each individual segment on a respective absorbent article. The device comprises a plurality of carrier units, each of which comprises a respective pad for transferring an individual segment from the cutting station to the applicator station. The transfer pad of each carrier unit performs a full rotation about a main axis of rotation to transfer the respective segment from the cutting station to the applicator station and return to the cutting station. The transfer pad of each carrier unit performs a rotation of at least 90° about its own axis of rotation from the cutting station to the applicator station to orient the segment in a direction transverse to the feed direction of the absorbent article.

The device comprises a first movement member for moving one or more carrier units about the main axis of rotation and a second movement member for moving one or more carrier units, separately from the carrier units moved by the first movement member, about the main axis of rotation.

Advantageously, the device allows attaining working speeds at least equal to 1000 ppm and controlling the movement of the carrier units through laws of motion implemented by the first and second movement means without replacing any other mechanical motion transmission parts.

BRIEF DESCRIPTION OF THE DRAWINGS

Further features and advantages of the invention are more apparent from the non-limiting description which follows of a preferred embodiment of a device as illustrated in the accompanying drawings, in which.

DETAILED DESCRIPTION OF PREFERRED EMBODIMENTS OF THE INVENTION

Figure 1:
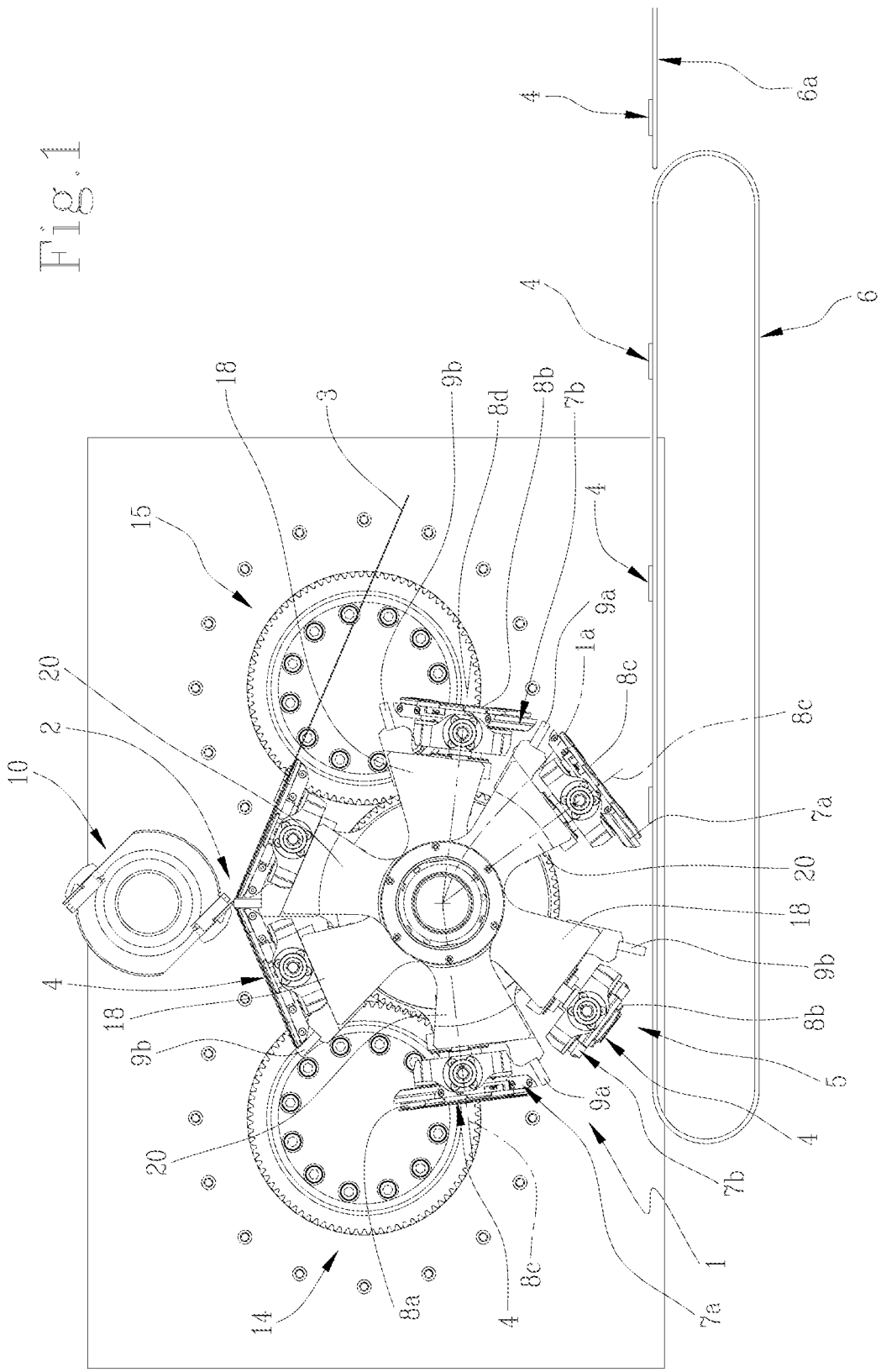
FIG. 1 is a schematic front view, with some parts cut away to better illustrate others, of the device according to this invention for applying segments of absorbent articles.
Figure 2:
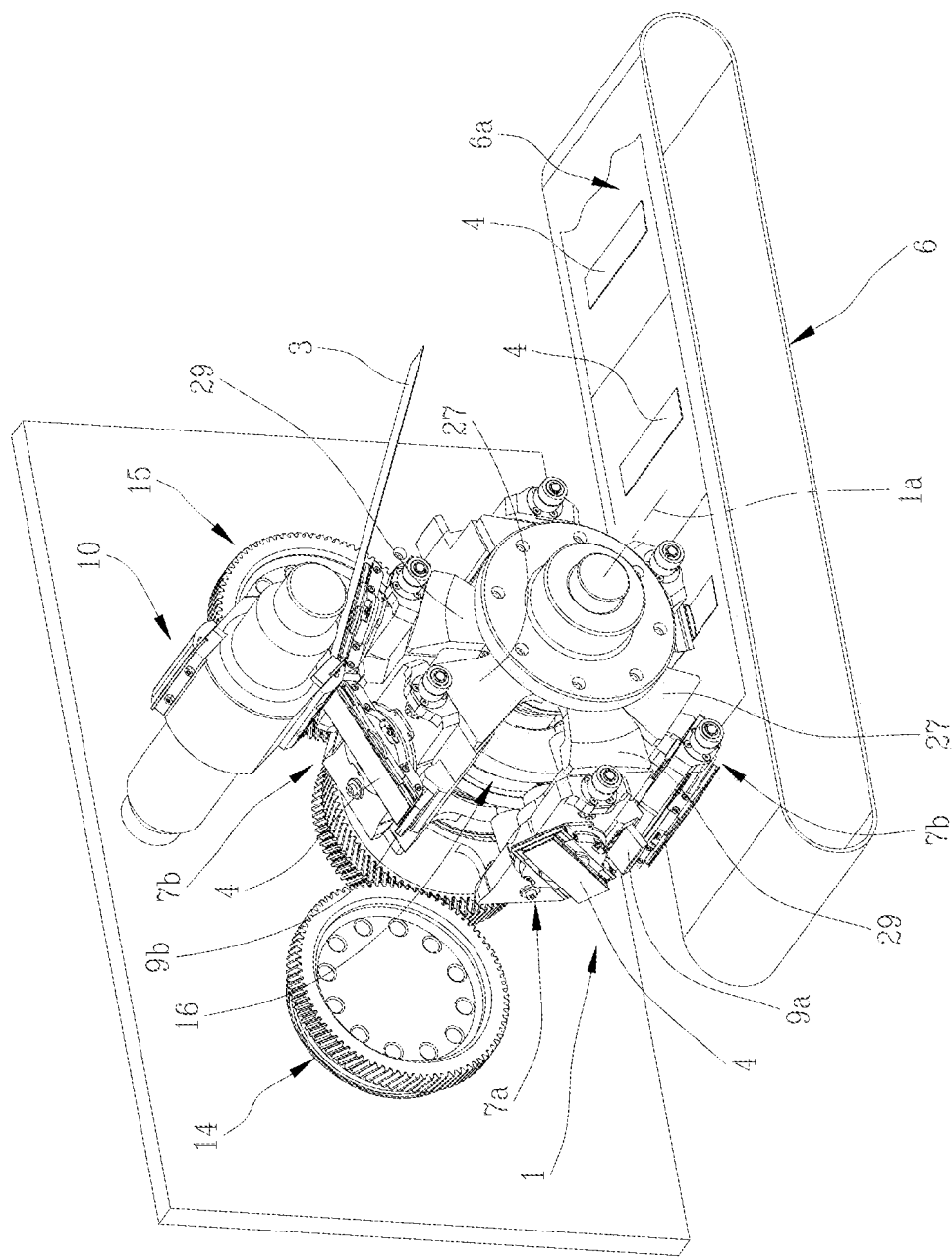
FIG. 2 shows the device of FIG. 1 in a schematic perspective view.
Figure 3:
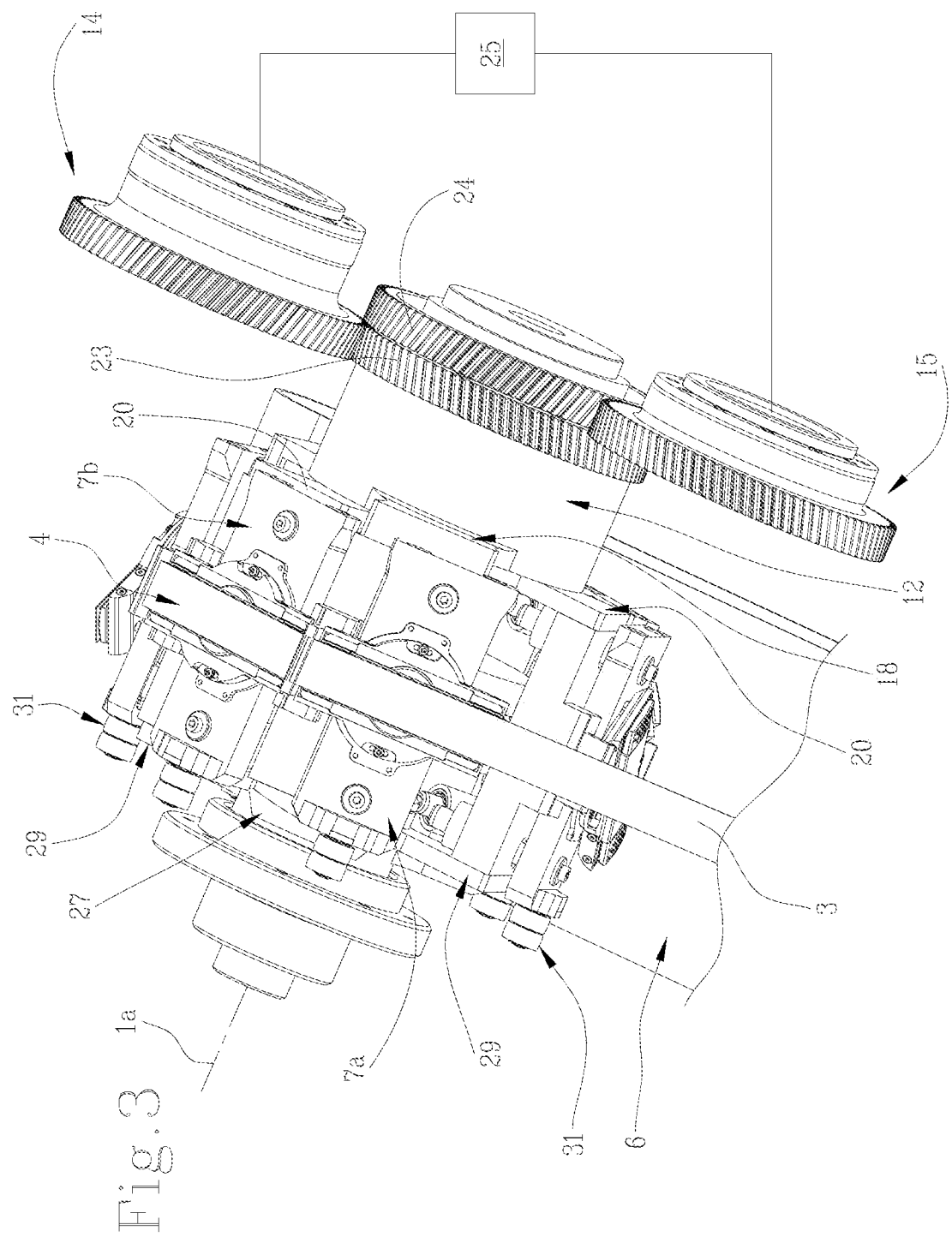
FIG. 3 shows the device of FIG. 1 in a schematic perspective view from above, with some parts cut away in order to better illustrate others.
Figure 4:
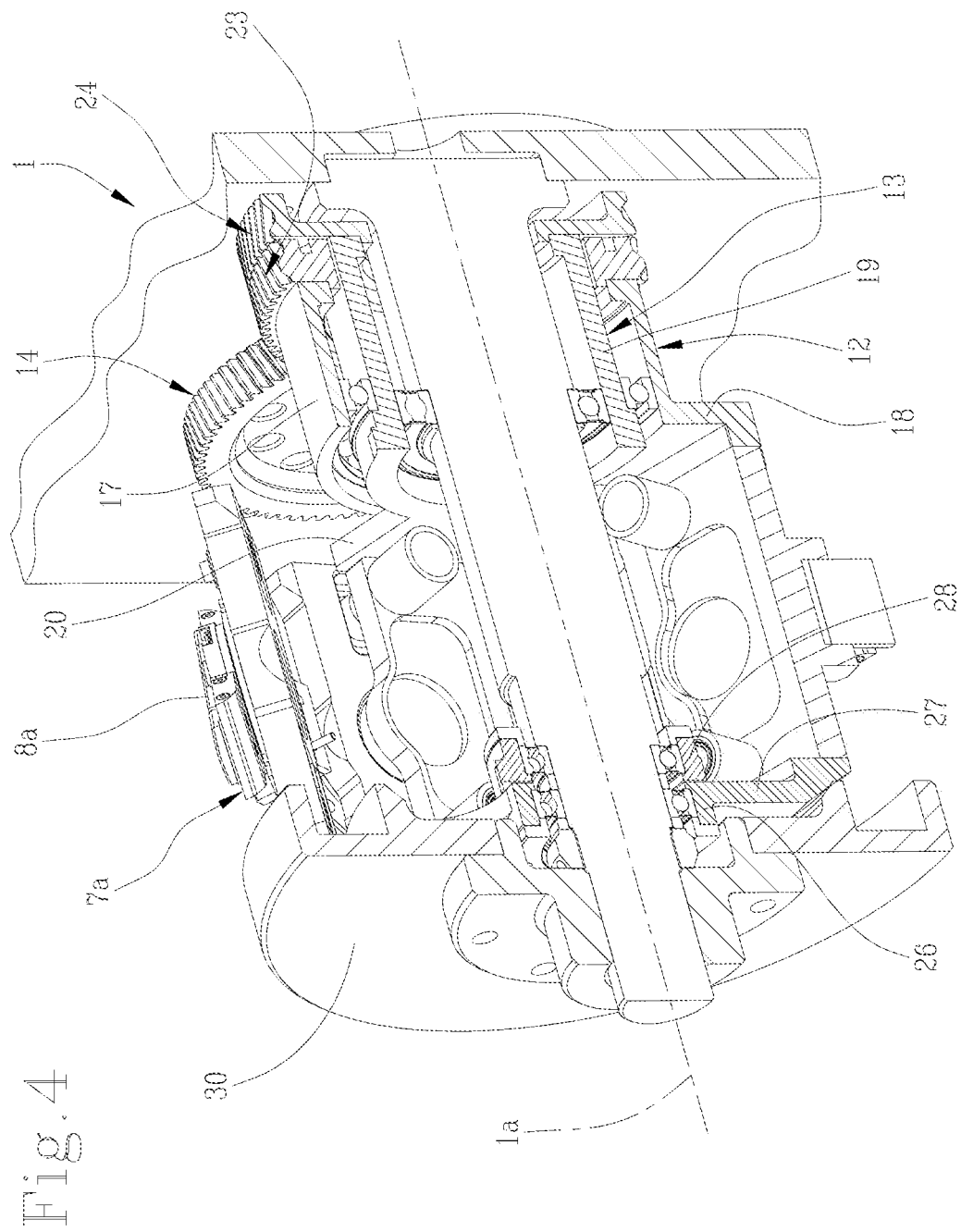
FIG. 4 shows the device of FIG. 1 in a schematic, cross-section perspective view, with some parts cut away in order to better illustrate others.

With reference to the accompanying drawings, the numeral 1 denotes in its entirety a device for applying segments of absorbent articles.

The device 1 comprises a cutting station 2 for cutting a continuous web 3 into individual segments 4 and an applicator station 5 for applying the individual segment 4 on a respective absorbent article 6a.

A feed line 6 for feeding the absorbent articles 6a is located downstream of the device 1 for applying the segments 4.

Generally speaking, the feed speed of the continuous web 3 is different from the feed speed of the absorbent articles 6a on which the respective segments 4 are applied.

More specifically, the feed speed of the continuous web 3 is less than the feed speed of the absorbent articles 6a.

For example, the term segment 4 is used to mean a piece of elasticized material used to form the waistband of a nappy for a child or adult.

The device 1 comprises a plurality of carrier units 7a, 7b for transferring a respective segment 4 from the cutting station 2 to the applicator station 5.

Each carrier unit 7a, 7b comprises a respective pad 8a, 8b for holding a respective segment 4 by its outside while it is being transferred from the cutting station 2 to the applicator station 5.

More specifically, each pad 8a, 8b holds the respective segment 4 by its outside surface by suction.

For this purpose, each carrier unit 7a, 7b comprises respective suction means, not illustrated, allowing the respective pad 8a, 8b to hold the segments 4.

Each carrier unit 7a, 7b of the device 1 is configured to rotate about a main axis of rotation 1a to transfer a respective segment 4 from the cutting station 2 to the applicator station 5 and back to the cutting station 2, thus completing a full rotation.

The cutting station 2 for cutting the continuous web 3, from which each single segment 4 is derived, and the applicator station 5 for applying the segment 4 are preferably angularly spaced by 180° so that the path followed by each carrier unit 7a and 7b from the moment it retains the cut segment 4 to the moment it releases it is the same length as the path each carrier unit 7a and 7b follows from the moment it releases the cut segment 4 to the moment it retains another cut segment 4 to be transferred.

Each carrier unit 7a, 7b of the device 1 comprises a respective anvil member 9a, 9b configured to act in conjunction with a cutting member 10 for cutting the continuous web 3 into the individual segments 4.

The cutting member 10 preferably comprises a roller which rotates about its axis of rotation and which is provided with one or more cutting edges disposed around its peripheral surface.

The anvil member 9a, 9b rotates about the main axis 1a of the device 1 as one with the respective carrier unit 7a, 7b.

More specifically, as it rotates about the main axis of rotation 1a, the anvil member 9a, 9b of each carrier unit 7a, 7b remains at a fixed position relative to the axis of rotation 1a.

Once the segment 4 has been cut off, each individual segment 4 must be oriented in such a way that it can be correctly applied to the absorbent article 6a. For this purpose, the pad 8a, 8b of each carrier unit 7a, 7b is configured to rotate about its own axis of rotation 8c, 8d, which is preferably radial to the main axis of rotation 1a of the device 1.

The axis of rotation 8c, 8d of the respective pad 8a, 8b may be barycentric relative to the pad 8a, 8b itself.

Alternatively, the axis of rotation 8c, 8d of the respective pad 8a, 8b is eccentric relative to the barycentric position of the pad 8a, 8b itself.

The axes of rotation 8c, 8d of the respective pads 8a, 8b of the device 1 may meet at a common point of origin on the main axis of rotation 1a or, alternatively, they may not meet at any point, in which case, the axes of rotation 8c, 8d of the respective pads 8a, 8b of the device 1 are skew relative to the main axis of rotation 1a.

Each pad 8a, 8b of the device 1 is configured to rotate through at least 90° from the cutting station 2 to the applicator station 5 and through at least 90° from the applicator station 5 to the cutting station 2 to return to its starting position.

With reference to the cutting station 2, in order for the cut to be made correctly, at least two pads 8a and 8b of two consecutive carrier units 7a and 7b must define as smooth a surface as possible for the continuous web 3 to lie and be held down on.

More specifically, the starting position of the outside surface of the pad 8a and 8b is parallel to the surface the web 3 is lying on.

At the moment of cutting, at least one anvil member 9a or 9b of a respective carrier unit 7a or 7b is positioned at the surface on which the web 3 is lying.

Once the segment 4 has been made by cutting the continuous web 3, each pad 8a, 8b rotates on itself about the respective axis of rotation 8c, 8d in order to orient each segment 4 transversely relative to the absorbent article 6a it is to be applied on.

Preferably, from the cutting station 2 to the applicator station 5, each pad 8a, 8b rotates on itself through at least 90° about its axis of rotation 8c, 8d.

This allows orienting each single segment 4 by placing it on the plane of the line of feed 6 of the absorbent articles 6a, perpendicularly to the feed direction of the absorbent articles 6a.

From the applicator station 5 to the cutting station 2, each pad 8a, 8b rotates on itself through a further 90° about its axis of rotation 8c, 8d to return to its starting configuration in the cutting station 2.

Thus, for each complete rotation about the main axis of rotation 1a, each pad 8a, 8b rotates on itself through at least 180° about its axis of rotation 8c, 8d.

In the same way, each pad 8a, 8b might rotate on itself through 90° first in one direction and then through the same angle in the opposite direction. This allows placing the pad 8a, 8b in the starting configuration again and resulting in a sum of rotation of 0°.

The pads 8a, 8b of respective carrier units 7a, 7b are driven rotationally about the respective axes of rotation 8c, 8d by cam means 16.

With reference to each carrier unit 7a, 7b, the respective pad 8a, 8b is movable radially towards and away from the main axis of rotation 1a in order to prevent possible interference with the respective anvil member 9a, 9b connected to the same carrier unit 7a, 7b during the rotation of the pad 8a, 8b about its own axis of rotation 8c, 8d.

From the cutting station 2 to the applicator station 5, the pads 8a, 8b of each carrier unit 7a, 7b pass from a respective starting position, where they are substantially tangent to the continuous web 3, to a raised position, at the applicator station 5, where they are substantially tangent to the absorbent article 6a which the segment 4 held by the respective pad 8a, 8b is applied on.

Downstream of the applicator station 5, each pad 8a, 8b passes from the raised position to the starting position, which it adopts again at the cutting station 2.

More specifically, from the starting position to the raised position, and vice versa, each pad 8a, 8b is movable along a radial direction relative to the main axis of rotation 1a of the device 1.

In other words, from the starting position to the raised position, and vice versa, each pad 8a, 8b is movable towards and away from the main axis of rotation 1a of the device 1.

More precisely, each pad 8a, 8b passes from the starting position to the raised position, away from the main axis of rotation 1a, and from the raised position to the starting position, towards the main axis of rotation 1a of the device 1.

By raised position is meant a position where each pad 8a, 8b is disposed at an operating circle on the outside of the operating circle of the anvil member 9a, 9b of the respective carrier unit 7a, 7b.

The to and fro movement of the pads 8a, 8b is determined by cam means 30, specifically a flat cam.

A coaxial cam follower roller bearing 31 is associated with a respective pad 8a, 8b to engage the cam means 30.

Cam means 16 determine the rotational movement of the pads 8a, 8b about the respective axes of rotation 8c, 8d whatever radial position they are at relative to the main axis of rotation 1a.

A fluted or lobed shaft, not illustrated, associated with a respective pad 8a, 8b, is engaged with the cam means 16.

With reference to what has been described up to now, it should be noted that for each complete rotation of each carrier unit 7a, 7b about the main axis of rotation 1a, each pad 8a, 8b of the respective movement member 12 and 13 performs at least three movements: a first rotational movement about the common axis of rotation 1a, a second rotational movement on itself about its own axis of rotation 8c, 8d and a third to and fro movement towards and away from the main axis of rotation 1a.

For each complete rotation of each pad 8a, 8b about the main axis of rotation 1a, preferably two of these three movements of the pad 8a, 8b are performed simultaneously.

More specifically, during the movement of each pad 8a, 8b away from the main axis of rotation 1a, the pad 8a, 8b rotates on itself through at least 90° about the respective axis 8c, 8d to orient the respective segment 4 in a direction transverse to the feed direction of the absorbent article 6a which it is to be applied on.

During the movement of each pad 8a, 8b towards the main axis of rotation 1a, the pad 8a, 8b rotates on itself through at least 90° about the respective axis 8c, 8d to orient the surface of the pad 8a, 8b in the desired direction, specifically relative to the feed direction the continuous web 3.

Since, with respect to the speed of the line of feed 6 of the absorbent articles 6a, the feed speed of the continuous web 3 is less than the feed speed of the absorbent articles 6a, each pad 8a, 8b has a first tangential speed v1, at the cutting station 2, and a second tangential speed v2, higher than the first speed v1, at least at the respective applicator station 5.

In this regard, attention is drawn to the following: the tangential, or peripheral, speeds v1 and v2 are determined by two variables related to the dynamics of the device 1: one variable is the angular speed "w" of the pad 8a, 8b and the other is the distance of the pad when it is furthest from the main axis of rotation 1a.

More precisely, each pad 8a, 8b has a first angular speed w1, at the cutting station 2, and a second angular speed w2, higher than the first rotation speed w1, at least at the respective applicator station 5.

According to this invention, the device 1 comprises a first movement member 12 for moving one or more carrier units 7a about the main axis of rotation 1a and a second movement member 13 for moving one or more carrier units 7b, separately from the carrier units 7a moved by the first movement member 12, about the main axis of rotation 1a.

The first movement member 12 comprises a respective drum 17, which rotates about the main axis of rotation 1a, and the second movement member 13 comprises a respective drum 19, which rotates about the main axis of rotation 1a and which is housed at least partly in the drum 17 of the first movement member 12.

In other words, the drum 17 of the first movement member 12 and the drum 19 of the second movement member 13 are concentric with each other relative to the main axis of rotation 1a.

The first movement member 12 comprises a plurality of spokes 18, connected to the drum 17 and each supporting a respective carrier unit 7a.

The carrier units 7a driven in rotation by the first movement member 12 are linked to each other in their rotation about the main axis of rotation 1a through the spokes 18 connected to the respective drum 17.

The spokes 18 are driven in rotation about the main axis 1a by the drum 17 of the first movement member 12.

Each spoke 18 is in the form of an arm extending radially with respect to the main axis of rotation 1a.

More specifically, the first movement member 12 comprises three spokes 18, connected to the drum 17 and each supporting a respective carrier unit 7a.

The spokes 18 are disposed relative to each other in such a way that two consecutive spokes 18 make an angle of 120°.

The first movement member 12 comprises an idler drum 26 and a plurality of spokes 27, connected to the drum 26 and each supporting a respective carrier unit 7a.

That way, each carrier unit 7a, driven by the first movement member 12, is supported by a respective pair of spokes 18, 27 set opposite and parallel to each other.

The second movement member 13 comprises a plurality of spokes 20, connected to the drum 19 and each supporting a respective carrier unit 7b.

The carrier units 7b driven in rotation by the second movement member 13 are linked to each other in their rotation about the main axis of rotation 1a through the spokes 20 connected to the respective drum 19.

The spokes 20 are driven in rotation about the main axis 1a by the drum 19 of the second movement member 13.

Each spoke 20 is in the form of an arm extending radially with respect to the main axis of rotation 1a.

More specifically, the second movement member 13 comprises three spokes 20, connected to the drum 19 and each supporting a respective carrier unit 7b.

The spokes 20 are disposed relative to each other in such a way that two consecutive spokes 20 make an angle of 120°.

The second movement member 13 comprises an idler drum 28 and a plurality of spokes 29, connected to the drum 28 and each supporting a respective carrier unit 7b.

That way, each carrier unit 7b, driven by the second movement member 13, is supported by a respective pair of spokes 20, 29 set opposite and parallel to each other.

The carrier units 7a, 7b driven by the first movement member 12 and by the second movement member 13 are mounted in such a way as to be disposed alternately to each other.

That way, at the cutting station 2 and at the applicator station 5, the transit of a carrier unit 7a supported by a spoke 18 of the drum 17 of the first movement member 12 is alternated with the transit of a carrier unit 7b supported by a spoke 20 of the drum 18 of the second movement member 13.

According to the invention, the device 1 comprises a first drive unit 14 for driving the first movement member 12 about the main axis of rotation 1a and a second drive unit 15 for driving the second movement member 13 about the main axis of rotation 1a separately from the first drive unit 14.

The device 1 comprises a control unit 25 configured to control and coordinate the movement of the first and second drive units 14, 15 in such a way that the pad 8a, 8b of the respective carrier unit 7a, 7b of the first and the second movement member 12, 13 have a first angular speed w1 about the main axis of rotation 1a at the cutting station 2 and, at the applicator station 5, a second angular speed w2 about the main axis of rotation 1a.

The control unit 25 is configured to be programmed by an operator. More specifically, the control unit 25 is configured to be programmed with the law of motion that the first and second drive units 14, 15 have to follow.

It should be noted that, with reference to a complete rotation about the main axis of rotation 1a, the laws of motion of the first and second drive units 14, 15 are identical.

The control unit 25 is configured to drive and coordinate the first and second drive units 14, 15 as a function of the law of motion they are programmed with.

Advantageously, the possibility of programming the law of motion of the control unit 25 allows changing the second angular speed w2 of the pad 8 as a function of the size of the absorbent article 6a.

Advantageously, for each changeover to a different size of absorbent article 6a, it is not necessary to replace the cam means 16 which rotationally drive the pads 8a, 8b of the respective carrier units 7a, 7b about the respective axes 8c, 8d and the cam means 30 which control the to and fro movement of the pads 8a, 8b towards and away from the main axis of rotation 1a.

In the embodiment illustrated, the first and second drive units 14, 15 are eccentric to the main axis of rotation 1a of the first and second movement members 12, 13.

Respective motion transmission means 23, 24 connect the first and second drive units 14, 15 to the first and second movement members 12, 13, respectively.

Preferably, the first and second drive units 14, 15 comprise respective torque motors which allow reaching the torques required by the application.

Alternatively, the first and second drive units 14, 15 are coaxial with the main axis of rotation 1a of the first and second rotating members 12, 13.

In a further, alternative embodiment, the first and second drive units 14, 15 comprise respective brushless motors, operating at constant rotation speed, and transmission means, preferably with non-circular gears, for transmitting motion to the first and second movement members 12, 13.

In this variant, the motion transmission means must be replaced at each changeover to a different size of absorbent article 6a.

In use, with reference to the cutting station 2, the retaining surfaces of the pads 8a, 8b of the respective carrier units 7a, 7b, which receive and retain the continuous web 3 while it is being cut by the cutting means 10, are oriented in a desired direction relative to the feed direction of the continuous web 3.

The pads 8a and 8b of the carrier units 7a and 7b which receive the continuous web 3 together form a smooth, uninterrupted surface for the web to lie and be held down on.

At the cutting station 2, the web 3 is cut into individual segments 4 by the cutting member 10, which operates on the surface of the anvil member 9a or 9b of the respective carrier unit 7a, 7b that receives the continuous web 3, driven in rotation about the main axis of rotation 1a towards the cutting station 2 at the first angular speed w1.

With reference to the first movement member 12, it should be noted that the carrier units 7a connected to the carrier unit 7a that is driven in rotation at the first angular speed w1 towards the cutting station 2 are also driven in rotation at a first speed w1 about the main axis 1a by the drum 17 which the supporting spokes 18 are connected to.

The same consideration applies to the second movement member 13, in the sense that the carrier units 7b connected to the carrier unit 7b that is driven in rotation at the first angular speed w1 towards the cutting station 2 are also driven in rotation at a first speed w1 about the main axis 1a by the drum 19 which the supporting spokes 20 are connected to.

Once the segment 4 has been obtained from the continuous web 3, the pad 8a. 8b starts moving relative to the respective anvil member 9a, 9b of the same carrier unit 7a, 7b away from the main axis of rotation 1a.

As stated above, the pad 8a, 8b moves away from the main axis of rotation 1a in a radial direction and, at the same time, rotates on itself about its own axis 8c, 8d to orient the segment 4 according to a position transverse to the feed direction of the absorbent article 6a.

As stated above, the pad 8a, 8b rotates about its axis of rotation 8c, 8d while it moves away from the main axis of rotation 1a.

At this point, the carrier unit 7a, 7b is accelerated and made to rotate about the main axis of rotation 1a towards the applicator station 5 at the second angular speed w2, which is equal to the feed speed of the absorbent articles 6a.

With reference to the first movement member 12, it should be noted that the carrier units 7a connected to the carrier unit 7a that is accelerated in rotation about the main axis of rotation 1a to reach the second angular speed w2 are also accelerated in rotation about the main axis 1a, to reach the second angular speed w2, by the drum 17 which the supporting spokes 18 are connected to.

This operating mode also applies to the carrier units 7b driven by the second movement member 13.

With reference to the second movement member 13, it should be noted that the carrier units 7b connected to the carrier unit 7b that is accelerated in rotation about the main axis of rotation 1a to reach the second angular speed w2 are also accelerated in rotation about the main axis 1a, to reach the second angular speed w2, by the drum 19 which the supporting spokes 20 are connected to.

At the applicator station 5, the carrier unit 7a, 7b is driven in rotation about the main axis of rotation 1a at the second angular speed w2.

With reference to the first movement member 12, it should be noted that the carrier units 7a connected to the carrier unit 7a that is driven in rotation about the main axis of rotation 1a at the second angular speed w2 are also driven in rotation about the main axis 1a at the second angular speed w2, by the drum 17 which the supporting spokes 18 are connected to.

This operating mode also applies to the carrier units 7b driven by the second movement member 13.

With reference to the second movement member 13, it should be noted that the carrier units 7b connected to the carrier unit 7b that is driven in rotation about the main axis of rotation 1a at the second angular speed w2 are also driven in rotation about the main axis 1a at the second angular speed w2, by the drum 19 which the supporting spokes 20 are connected to.

At the applicator station 5, the pad 8a, 8b of the respective carrier unit 7a, 7b is disposed at a position substantially tangent to the absorbent article 6a so as to release and apply the segment 4 conveyed in a direction transverse to the feed direction of the absorbent article 6a.

Once the pad 8a, 8b has released the respective segment 4, the respective carrier unit 7a, 7b decelerates to return to the first feed speed v1 of the web 3.

With reference to the first movement member 12, it should be noted that the carrier units 7a connected to the carrier unit 7a that is decelerated in rotation about the main axis of rotation 1a are also decelerated in rotation by the drum 17 which the supporting spokes 18 are connected to.

This operating mode also applies to the carrier units 7b driven by the second movement member 13.

With reference to the second movement member 13, it should be noted that the carrier units 7b connected to the carrier unit 7b that is decelerated in rotation about the main axis of rotation 1a are also decelerated in rotation by the drum 19 which the supporting spokes 20 are connected to.

At this point, the pad 8a, 8b moves towards the main axis of rotation 1a in a radial direction.

As the pad 8a, 8b moves towards the main axis of rotation 1a, the pad 8a, 8b rotates on itself through 90° about its own axis 8c, 8d to return the respective retaining surface to the correct orientation relative to the feed direction of the web 3, for example in a direction parallel to the feed direction of the web 3.

At the cutting station 2, the carrier unit 7a, 7b of the respective movement member 12, 13 is driven in rotation about the main axis of rotation 1a at the first angular speed w1.

It should be noted that, with reference to the path followed by the carrier units 7a, 7b of the device 1 from the cutting station 2 to the applicator station 5, and vice versa, the first and second drive units 14, 15, driven and coordinated by the control unit 25, drive the first and the second movement member 12, 13, respectively, in such a way as to drive the respective carrier unit 7a, 7b in rotation about the main axis of rotation 1a at the first angular speed w1 to the cutting station 2 and at the second angular speed w2 to the applicator station 5.

The carrier units 7a, 7b connected to the same movement member 12, 13 simultaneously follow the movement transmitted by the first and the second movement member 12, 13, respectively, as a function of the law of motion of the control unit 25.

Lastly, with reference to the embodiment illustrated, in which the first movement member 12 comprises three spokes 18 disposed relative to each other in such a way that two consecutive spokes 18 make an angle of 120°, it should be noted that when a carrier unit 7a, supported by a respective spoke 18, passes through the cutting station 2, none of the other carrier units 7a connected to it, passes through the applicator station 5.

The same reasoning applies to the applicator station 5: that is to say, when a carrier unit 7a, supported by a respective spoke 18, passes through the applicator station 5, none of the other carrier units 7a connected to it, passes through the cutting station 2.

The above also applies to the second movement member 13, comprising three spokes 20 disposed relative to each other in such a way that two consecutive spokes 20 make an angle of 120°: when a carrier unit 7b, supported by a respective spoke 20, passes through the cutting station 2, none of the other carrier units 7b connected to it, passes through the applicator station 5.

The same reasoning applies to the applicator station 5: that is to say, when a carrier unit 7b, supported by a respective spoke 20, passes through the applicator station 5, none of the other carrier units 7b connected to it, passes through the cutting station 2.

The invention claimed is:

1. A device for applying segments of absorbent articles, comprising:
    a cutting station for cutting a continuous web into individual segments;
    an applicator station for applying each individual segment on a respective absorbent article;
    a plurality of carrier units, each of which comprises a transfer pad for retaining and transferring an individual segment from the cutting station to the applicator station;
    the transfer pad of each carrier unit configured to perform a full rotation about a main axis of rotation to transfer the individual segment from the cutting station to the applicator station and return to the cutting station;
    the transfer pad of each carrier unit configured to perform a rotation of at least 90° about its own axis of rotation from the cutting station to the applicator station to orient the individual segment in a direction transverse to a feed direction of the absorbent article;
    during a rotation of the carrier unit about the main axis of rotation, each transfer pad is configured to move radially towards and away from the main axis of rotation;
    a first movement member configured for moving one or more of the carrier units about the main axis of rotation and a second movement member configured for moving one or more of the carrier units, separately from the one or more carrier units moved by the first movement member, about the main axis of rotation;
    the first movement member comprising a first drum, which rotates about the main axis of rotation, and the second movement member comprising a second drum, which rotates about the main axis of rotation and which is housed at least partly in the first drum.

2. The device according to claim 1, and further comprising a first drive unit configured for driving the first movement member about the main axis of rotation and a second drive unit configured for driving the second movement member about the main axis of rotation separately from the first drive unit.

3. The device according to claim 2, and further comprising a control unit configured to control and coordinate the movement of the first and second drive units such that the transfer pad of the respective carrier unit of the first and the second movement member has a first speed of rotation about the main axis of rotation at the cutting station and, at the applicator station, a second speed of rotation about the main axis of rotation different from the first speed of rotation.

4. The device according to claim 3, wherein the control unit is configured to be programmed to provide motion paths of the first and second drive units.

5. The device according to claim 1, wherein the first movement member comprises a plurality of spokes, each supporting a respective carrier unit and driven in rotation by the first drum.

6. The device according to claim 1, wherein the second movement member comprises a plurality of spokes, each supporting a respective carrier unit and driven in rotation by the second drum.

7. The device according to claim 1, wherein the carrier units of the first movement member and of the second movement member are mounted to be disposed alternately to each other; at the cutting station and at the applicator station, a transit of a carrier unit supported by a spoke of the first drum being alternated with a transit of a carrier unit supported by a spoke of the second drum.

8. The device according to claim 1, wherein the first and second movement members each comprise three respective spokes; the spokes of the respective first and second movement members being disposed relative to each other such that two consecutive spokes make an angle of 120°.

9. The device according to claim 1, wherein each carrier unit comprises a respective anvil member for cutting the continuous web; with reference to rotation about the main axis of rotation, the anvil member being fixed to the carrier unit.

10. The device according to claim 9, wherein, the anvil member remains at a fixed radial position relative to the main axis of rotation as the transfer pad moves radially toward and away from the main axis of rotation.

\* \* \* \* \*